United States Patent [19]

Hegasy

[11] Patent Number: 4,892,730

[45] Date of Patent: Jan. 9, 1990

[54] PROCESSES FOR PREPARATION OF SOLID, RAPIDLY RELEASED MEDICAMENT PREPARATIONS CONTAINING DIHYDROPYRIDINES

[75] Inventor: Ahmed Hegasy, Leverkusen, Fed. Rep. of Germany

[73] Assignee: Bayer Aktiengesellschaft, Leverkusen, Fed. Rep. of Germany

[21] Appl. No.: 247,009

[22] Filed: Sep. 20, 1988

Related U.S. Application Data

[60] Division of Ser. No. 864,677, May 19, 1986, which is a continuation of Ser. No. 728,123, Apr. 29, 1985, abandoned, which is a continuation of Ser. No. 433,570, Oct. 8, 1982, abandoned.

[30] Foreign Application Priority Data

Oct. 29, 1981 [DE] Fed. Rep. of Germany ....... 3142853
Feb. 16, 1982 [DE] Fed. Rep. of Germany ....... 3205399

[51] Int. Cl.[4] ...................... A61K 31/78; A61K 31/44
[52] U.S. Cl. ......................................... 424/80; 514/356
[58] Field of Search ........................................... 424/80

[56] References Cited

U.S. PATENT DOCUMENTS 4,216,155 8/1980 Haas et al. ........................... 514/826
4,412,986 11/1983 Kawata et al. ...................... 514/356

OTHER PUBLICATIONS

Chemical Abstracts; vol. 83 (1975) #209407w; Kramer et al.
Chemical Abstracts; vol. 90 (1979) #109,987m; Kawata et al.

*Primary Examiner*—Douglas W. Robinson
*Assistant Examiner*—Joseph A. Lipovsky
*Attorney, Agent, or Firm*—Sprung, Horn, Kramer & Woods

[57] ABSTRACT

Solid dihydropyridines, e.g. nifedipine and nimodipine preparations having a maximum standard deviation of the active compound content of 3% contain 1 part by weight of nifedipine, 2 to 6 parts by weight of PVP with a mean molecular weight of 15,000 to 50,000, 3.5 to 15 parts by weight of cellulose, 0.25 to 4 parts by weight of starch and 0.5 to 4 parts by weight of cross-linked insoluble PVPP, and, if appropriate, one or more further pharmaceutical auxiliaries and excipients. These preparations show a good release of dihydropyridine with good content uniformity.

12 Claims, No Drawings

PROCESSES FOR PREPARATION OF SOLID, RAPIDLY RELEASED MEDICAMENT PREPARATIONS CONTAINING DIHYDROPYRIDINES

This is a division of application Ser. No. 864,677 filed May 19, 1986, (now pending), which is a continuation of 728,123, filed 4/29/85, now abandoned, which is a continuation of application Ser. No. 433,570, filed 10/8/82 (now abandoned).

The present invention relates to certain novel special rapidly absorbable solid medicament preparations which contain dihydropyridines and polyvinylpyrrolidone, and to processes for their preparation.

Nifedipine (dimethyl 1,4-dihydro-2,6-dimethyl-4-(o-nitrophenyl)-pyridine-3,5-dicarboxylate) is a known active compound from the substance class of the dihydropyridines, which affects the circulation (see British Patent Specification No. 1,173,862). Owing to its extreme sensitivity to light and its extremely low solubility in aqueous media, a number of difficulties occur in the pharmaceutical preparation of special medicaments, as is evident from numerous patent applications and patents for special formulations of this active compound.

U.S. Pat. No. 3,784,684 relates, for example, to special gelatine bitable capsules which contain nifedipine in dissolved form, in order advantageously to utilise the coronary action of nifedipine.

British Patent Specification No. 1,456,618 describes and claims solid medicament preparations which are intended to ensure good bio-availability of the nifedipine.

DE-OS (German Published Specification) 2,822,882 likewise describes solid medicament preparations in which the poor solubility of nifedipine is to be compensated by the use of certain solvents and surface-active substances.

In European Published Patent Application No. 1,247, it is also intended to improve the absorbability of nifedipine by the use of polyethylene glycol (PEG) and certain porous excipients In this application, it is also stated that the poor solubility of nifedipine can be compensated by the formation of coprecipitates of nifedipine and polyvinylpyrrolidone (PVP), in which coprecipitates the nifedipine is present in amorphous form.

These coprecipitates are prepared by dissolving nifedipine and PVP in organic solvents and subsequently evaporating the solvent to obtain a glassy mass (see DE-OS (German Published Specification) No. 2,822,882). Such an evaporation of the organic solvent can be carried out industrially only at great expense, since the PVP mass binds the organic solvent strongly and becomes very viscous shortly before drying. A voluminous foamy mass is formed which is very viscous shortly before the end of the drying procedure, can no longer be stirred, and is difficult to process further. A further disadvantage in the use of customary PVP coprecipitates in the production of tablets is the fact that this coprecipitate can only be mixed with other auxiliaries but can no longer be directly granulated with aqueous solutions. However, such a simple mixture of the PVP coprecipitate with other auxiliaries tends to separate during further mechanical processing, for example to give tablets or during introduction into capsules. This can finally lead to medicament preparations with very variable active compound contents in the individual tablets or capsules (deficient "content uniformity"), which is extremely undesirable in the case of a highly active substance such as nifedipine. Moreover, the additional auxiliaries which may be chosen are very limited, in particular for the production of tablets, because PVP simultaneously acts as a binder, and the disintegration of the tablets or capsules is hindered by the presence of large amounts of PVP (30-100 mg per tablet or capsule).

Nimodipine (1,4-dihydro-2,6-dimethyl-4-(3'-nitrophenyl)-pyridine 3-methoxyethyl ester 5-isopropyl ester) is likewise a known dihydropyridine with a cerebral action (see DOS (German Published Specification) No. 2,815,578). This compound also is difficult to process to give pharmaceutical preparation forms, owing to its physico-chemical properties. Nimodipine has, for example, a substantially poorer solubility than nifedipine in aqueous media.

The present invention relates to new solid rapidly released preparations containing dihydropyridines, and processes for their preparation, which no longer have these disadvantages of the preparations known hitherto.

According to the present invention there are provided rapidly absorbable, solid medicament preparations with a uniform active compound content, the relative standard deviation of which is at most 3%, preferably at most 2.5%, comprising 1 part by weight of dihydropyridine as active compound, 2.0 to 6.0 parts by weight of PVP having a mean molecular weight of 15,000 to 50,000, and absorptive excipients consisting of from 3.5 to 15 parts by weight of cellulose, 0.25 to 4.0 parts by weight of starch and 0.25 to 4.0 parts by weight of crosslinked insoluble PVPP, and comprising if appropriate, further formulation auxiliaries and/or excipients. The abbreviation "PVPP" used herein stands for cross-linked insoluble polyvinyl-pyrrolidone, such as Polyplasdone XL ® from GAF Corp., New York, N.Y. USA or KOLLIDONE CL ® from BASF, Ludwigshafen, Germany.

These solid medicament preparations are prepared by a process in which 1 part by weight of dihydropyridine and 2 to 6 parts by weight of PVP are dissolved in a small amount of organic solvent in which the two solid constiuents are just soluble, and this solution is granulated with 4 to 23 parts by weight, preferably with 5.5 to 17 parts by weight, of the abovementioned excipients, and these granules are then processed further, if desired, with further formulation auxiliaries and/or excipients to give solid medicament preparations.

The following may preferably be mentioned as organic solvents: $C_1$-$C_3$-alkanols; $C_1$-$C_2$-dialkyl ketones; and chlorinated alkanes having 1-2 carbon atoms. Specific examples include ethanol, acetone, methylene chloride and chloroform, and in particular mixtures of these solvents. They are preferably employed in an amount of 2 to 20, in particular of 8 to 16, parts by weight, relative to the dihydropyridine.

A powder mixture of 4 to 12 parts by weight of cellulose, 0.25 to 2.0 parts by weight of starch and 1 to 3 parts by weight of crosslinked insoluble PVPP is particularly suitable as the said adsorptive excipient.

Preferred preparations according to the present invention are those in which the relative standard deviation of the active component content is at most 2.5% and 50% of the active compound is released in less than 30 minutes; especially those in which the active compound is nifedipine 50% of which is released in less than 15 minutes.

The following may preferably be mentioned as customary auxiliaries and excipients which can be used for the active compound content (good content uniformity).

TABLE

| Example No. | Examples according to known methods | | | | | | Examples according to the invention | | | |
|---|---|---|---|---|---|---|---|---|---|---|
| | A | B | C | D | E | F | 1 | 2 | 3 | 4 |
| Standard deviation of the tablet weights | 1.7% | 1.0% | 1.1% | 1.7% | — | — | 1.0% | 0.7% | 0.7% | 0.8% |
| Deviation of the nifedipine content in mg in individual tablets (10 tablets) | 8.86–10.12 | 8.04–10.32 | 8.75–10.15 | 8.44–9.65 | 10.01–10.83 | 9.55–10.03 | 10.03–10.31 | 10.30–10.55 | 10.49–10.81 | 9.98–10.53 |
| Standard deviation of the nifedipine content per tablet | 4.1% | 6.7% | 5.1% | 4.7% | 2.4% | 1.8% | 1.0% | 0.774% | 1.088% | 1.413% |
| Nifedipine release* 50% released after (minutes) | appr. 10′ | appr. 10′ | appr. 10′ | appr. 10′ | <10′ | 30′–40′ | <5′ | <10′ | <10′ | <10′ |

*The release test is effected according to the USP Padelle method.

further processing to give solid medicament preparations: lactose, powdered sugar, mannitol, glycocoll and calcium carbonate.

The following may preferably be mentioned as solid medicament preparations: tablets, pills, dragees, granules, powders, capsules and sachets.

It could not be foreseen that the medicament preparations thus obtained would possess very good bio-availability and at the same time a good content uniformity. The granules obtained by the process according to the invention and consisting of the powder mixture wetted with active compound/PVP solution can, without problems, be dried, sieved, processed further, mixed with other auxiliaries and excipients and pressed to give tablets.

In view of thenumerous attempts, known from the prior art, to prepare suitable medicament preparations containing dihydropyridine, it could not be foreseen that new and valuable medicament preparations which contain these active compounds, which are distinguished by good bio-availability, and the active compound content of which only has a maximum standard deviation of 3%, preferably of 2.5%, would be obtained by the process according to the invention, which process can be carried out readily and without technical effort (see the textbook: Pharmazeutische Technologie (Pharmaceutical Technology), published by Sucker, Fuchs and Speises, page 32 to 37, and U.S. Pharmacopoea XX, page 955 to 957).

To demonstrate the advantageous properties of the best preparations prepared according to the invention, tablets were prepared, according to Examples A to F, by conventional methods in which a solid coprecipitate of nifedipine and PVP was first prepared by evaporating off the solvent, and these solid granules were then mixed with customary auxiliaries and excipients, and processed further to give solid tablets. In contrast, in Examples 1 to 8 according to the invention, the coprecipitate of nifedipine and PVP or of nimodipine and PVP was not isolated but was granulated as a solution with a mixture of solid excipients, and these granule were then pressed in the customary manner to give tablets.

The following table shows that the solid formulations according to the invention are very rapidly and completely absorbed (good release) and at the same time exhibit only a very low relative standard deviation of Examples of the Preparation of Solid Nifedipine Preparations According to Known Methods The mixtures of Examples A to F and Example 1 relate to the preparation of 10,000 tablets each. Examples 2 to 4 account for 15,000 tablets each.

EXAMPLE A 100 g of nifedipine and 400 g of PVP 25 (mean molecular weight 25,000) were dissolved in 1,500 g of methylene chloride. When the solvent was evaporated, a very viscous mass which could not be stirred was initially formed, and this mass became a foamy glassy mass after some time. This coprecipitate was brought to a maximum particle size of 1.0 mm via an oscillating sieve. In a separate operation, granules were prepared from 1,050 g of microcrystalline cellulose ("Avicel"—Trade Mark), 350 g of corn starch and 50 g of corn starch made into a paste with boiling water. These granules were mixed with 500 g of the nifedipine coprecipitate, with 4 g of magnesium stearate and 246 g of insoluble cross-linked PVP (e.g. Plasdone XL-Trade Mark, or Kollidon CL—Trade Mark). Tablets having a weight of 220 mg and a mean nifedipine contents of 10 mg were prepared from this mixture.

EXAMPLES B AND C

The coprecipitates prepared in the same manner as in A were brought, via an oscillating sieve, to a maximum particle size of 0.8 mm in the case of Example B or 0.6 mm in the case of Example C, and were then processed further, in the same manner as in Example A, to give tablets.

EXAMPLE D

The coprecipitate prepared analogously to Example A was comminuted by means of a hammer mill and then processed further, as in Example A, to give tablets.

EXAMPLE E 100 g of nifedipine and 400 g of PVP 25 were dissolved in 1,200 g of methylene chloride, and the solution was dried in vacuo. The coprecipitate obtained was mixed directly with granules which had been prepared from 100 g of cellulose, 450 g of starch and 50 g of starch made into a paste with boiling water, and with 5 g of magnesium stearate, 195g of starch and 200 g of insoluble polyvinylpyrrolidone, and this mixture was then pressed to give tablets weighing 240 mg.

EXAMPLE F

A coprecipitate prepared analogously to Example E was mixed directly with the mixture of cellulose and starch, was granulated with the starch paste (that is to say in an aqueous medium), and was then pressed to give tablets, analogously to Example E. Although the tablets prepared in this manner possessed an improved content uniformity, they gave unsatisfactory release values.

The following Examples illustrate medicaments and a process for their production according to the present invention.

EXAMPLE 1

100 g of nifedipine and 400 g of PVP 25 were dissolved in 1,800 of methylene chloride. In a granulating apparatus, 1,050 g of cellulose, 200 g of starch and 100 g of insoluble PVPP were mixed in the dry state and granulated with the nifedipine/PVP solution. The moist granules obtained were dried and sieved, 145 g of insoluble PVPP, 200 g of starch and 4 g of magnesium stearate were then added, the ingredients were mixed, and this mixture was pressed to give tablets of 220 mg. These tablets were distinguished by a very good content uniformity and advantageous release.

EXAMPLE 2

Analogously to Example 1, 150 g of nifedipine and 600 g of PVP 25 were dissolved in 1,800 g of methylene chloride, and this solution was granulated directly with a mixture of 1,575 g of microcrystalline cellulose ("Avicel") and 600 g of corn starch. After the granules had been dried and sieved, they were mixed with 6 g of magnesium stearate and 369 g of insoluble PVPP, and the mixture was pressed to give tablets weighing 220 mg.

EXAMPLE 3

Analogously to Example 2, 150 g of nifedipine and 600 g of PVP 25 were dissolved in 2,200 g of methylene chloride. The solution was granulated for granulating a mixture of 1,575 g of microcrystalline cellulose 600 g of corn starch and 300 g of insoluble PVPP. After the granules had been dried and sieved, they were mixed with 6 g of magnesium stearate and 69 g of insoluble PVPP, and the mixture was pressed to give tablets weighing 220 mg.

EXAMPLE 4

150 g of nifedipine and 600 g of PVP 25 were dissolved in 2,100 g of methylene chloride. This solution was used for granulating a mixture of 1,575 g of microcrystalline cellulose, 600 g of corn starch and 150 g of insoluble PVPP. After the granules had been dried and sieved, they were mixed with 66 g of magnesium stearate and 219 g of insoluble PVPP, and the mixture was pressed to give tablets weighing 220 mg.

EXAMPLE 5

The following amounts are calculated for the production of 100,000 tablets, each containing 10 mg of nifedipine: 1 kg of nifedipine and 4 kg of PVP 25 were dissolved in 7 kg of acetone. The solution was used for granulating a mixture of 10.5 kg of microcrystalline cellulose ("Avicel"), 2 kg of starch and 1 kg of insoluble PVPP. The mass was dried in vacuo, sieved, and mixed with 1.46 kg of insoluble PVPP, 2 kg of starch and 0.04 kg of magnesium stearate. The mixture was pressed to give tablets weighing 220 mg and having a diameter of 9 mm. 20 kg of tablets were sprayed with a suspension of 0.3 kg of hydroxypropylmethylcellulose, 0.1 kg of polyethylene glycol 4000, 0.09 kg of titanium dioxide and 0.01 kg of red iron oxide in 6.17 kg of water.

EXAMPLE 6

The following amounts are calculated for the production of 250,000 tablets, each containing 20 mg of nifedipine: 5 kg of nifedipine and 20 kg of PVP 25 were dissolved in a mixture of 35 kg of acetone and 10 kg of methylene chloride. The solution was used for granulating a mixture of 52.5 kg of microcrystalline cellulose, 10 kg of starch and 5 kg of insoluble PVPP. After the granules had been dried in vacuo and sieved, they were admixed with 7.3 kg of insoluble PVPP, 10 kg of starch and 0.2 kg of magnesium stearate. The mixture was pressed to give tablets weighing 440 mg. 100 kg of tablets were coated by spraying with a suspension of 1.5 kg of hydroxypropylmethylcellulose, 0.5 kg of PEG 4000, 0.4 kg of titanium dioxide, 0.1 kg of red iron oxide and 30.83 kg of water.

EXAMPLE 7

The following amounts are calculated for the production of 20,000 tablets, each containing 30 mg of nimodipine: 0.6 kg of nimodipine and 1.5 kg of PVP 25 were dissolved in 1.4 kg of acetoe. The solution was used for granulating a mixture of 2.85 kg of microcrystalline cellulose, 0.150 kg of starch and 0.6 kg of insoluble PVPP. The mass was dried in vacuo, sieved, and mixed with 0.288 kg of insoluble PVPP, 0.566 kg of starch and 0.011 kg of magnesium stearate. The mixture was pressed to give tablets weighing 330 mg and having a diameter of 10 mm. 6 kg of tablets were coated by spraying with a suspension of 0.225 kg of hydroxypropylmethylcellulose, 0.075 kg of polyethylene glycol 4000 and 0.075 kg of titanium dioxide in 4.625 kg of water. The analyses of the individual tablet content of nimodipine were between 29.78 mg and 31.18 mg, with a relative standard deviation of 1.156%.

EXAMPLE 8

A batch of 26.4 kg of tablet mixture, sufficient for 60,000 tablets, each containing 40 mg of nimodipine, was prepared in the following manner: 2.4 kg of nimodipine and 6.0 kg of PVP 25 were stirred in 5.76 kg of acetone until a clear viscous solution was present. 11.4 kg of microcrystalline cellulose, 0.6 kg of starch and 2.4 kg of insoluble PVPP were mixed in a granulating apparatus. The abovementioned solution containing nimodipine was then added. Afer this solution had been granulated with the powder constituents, the mass was dried in vacuo and then brought to a mean particle size of 1.0 mm diameter by sieving. For this purpose, 2.4 kg of starch, 1.152 kg of insoluble PVPP and 0.48 kg of magnesium stearate were mixed. Tablets having a weight of 440 mg were pressed from this mixture. 24 kg of these tablets were coated by spraying with a suspension of 0.54 kg of hydroxypropyl-methylcellulose, 0.18 kg of polyethylene glycol 4000 and 0.18 kg of titanium dioxide in 11.1 kg of water. The average content of nimodipine in the individual tablets was 40.5 mg. The relative standard deviation was 2.21%.

What is claimed is:

1. A process for the production of a solid medicament preparation, which process comprises dissolving 1 part by weight of dihydropyridine as active compound and 2.0 to 6.0 parts by weight of PVP having a mean molecular weight of 15,000 to 50,000, in 2 to 20 parts by weight of an amount of an organic solvent which is sufficient to dissolve the dihydropyridine and PVP, then granulating this resultant solution with 4 to 23 parts by weight of absorptive excipients comprising a mixture of 3.5 to 15 parts by weight cellulose, 0.25 to 4 parts by weight starch and 0.25 to 4 parts by weight crosslinked insoluble PVPP, then further processing the resulting granules to give the solid medicament preparation.

2. A process according to claim 1, in which 5.25 to 17 parts by weight of the said absorptive excipients are employed.

3. A process according to claim 1, in which the organic solvent is selected from ethanol, acetone, methylene chloride, chloroform, and mixtures of these solvents.

4. A process according to claim 1, which further comprises conducting the further processing of the resulting granules in the presence of further formulation auxiliaries and/or excipients.

5. A process according to claim 4, wherein the further formulation auxiliaries and/or excipients are selected form the group consisting of lactose, powdered sugar, mannitol, glycocoll and calcium carbonate.

6. A process according to claim 1, wherein the dihydropyridine is selected from the group consisting of nifedipine and nimodipine.

7. A process according to claim 1, wherein said dihydropyridine has a maximum relative standard deviation of 1.413%.

8. A process according to claim 1, wherein the active compound has a mean standard deviation of at most 2.5%.

9. A process according to claim 1, wherein the active compound is released in less than 30 minutes.

10. A process according to claim 1, wherein the absorptive excipients comprise a powder mixture of 4 to 12 parts by weight of cellulose, 0.25 to 2.0 parts by weight of starch and 1 to 3 parts by weight of crosslinked insoluble PVPP.

11. A process according to claim 1, wherein said dihydropyridine is nifedipine.

12. A process according to claim 1, wherein said dihydropyridine is nimodipine.

* * * * *